US009060998B2

(12) United States Patent
Stockfleth

(10) Patent No.: US 9,060,998 B2
(45) Date of Patent: *Jun. 23, 2015

(54) USE OF A POLYPHENOL FOR THE TREATMENT OF A CANCEROUS OR PRE-CANCEROUS LESION OF THE SKIN

(71) Applicant: MediGene AG, Planegg/Martinsried (DE)

(72) Inventor: Eggert Stockfleth, Albersdorf (DE)

(73) Assignee: Medigene AG, Planegg/Martinsfried (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/888,949

(22) Filed: May 7, 2013

(65) Prior Publication Data

US 2013/0245113 A1 Sep. 19, 2013

Related U.S. Application Data

(63) Continuation of application No. 13/051,593, filed on Mar. 18, 2011, now Pat. No. 8,455,022, which is a continuation of application No. 10/574,422, filed as application No. PCT/EP2004/011300 on Oct. 8, 2004, now Pat. No. 7,910,138.

(60) Provisional application No. 60/510,101, filed on Oct. 9, 2003.

(51) Int. Cl.
*A61K 36/00* (2006.01)
*A61K 36/82* (2006.01)
*A61K 31/353* (2006.01)
*A61K 31/7048* (2006.01)

(52) U.S. Cl.
CPC ........... *A61K 31/353* (2013.01); *A61K 31/7048* (2013.01); *A61K 36/82* (2013.01)

(58) Field of Classification Search
None
See application file for complete search history.

(56) References Cited

U.S. PATENT DOCUMENTS

| 4,002,775 A | 1/1977 | Kabara |
| 4,248,789 A | 2/1981 | Okada |
| 4,306,568 A | 12/1981 | Torre |
| 4,613,672 A | 9/1986 | Hara |
| 4,673,530 A | 6/1987 | Hara |
| 4,863,970 A | 9/1989 | Patel et al. |
| 4,913,909 A | 4/1990 | Hara et al. |
| 4,931,284 A | 6/1990 | Ekman et al. |
| 5,104,901 A | 4/1992 | Shimamura et al. |
| 5,135,957 A | 8/1992 | Shimamura |
| 5,137,922 A | 8/1992 | Shimamura et al. |
| 5,204,089 A | 4/1993 | Hara et al. |
| 5,306,486 A | 4/1994 | McCook et al. |
| 5,318,986 A | 6/1994 | Hara et al. |
| 5,358,713 A | 10/1994 | Shimamura |
| 5,470,565 A | 11/1995 | Hayakawa et al. |
| 5,633,284 A | 5/1997 | Meyer |
| 5,652,266 A | 7/1997 | Bobier-Rival et al. |
| 5,670,154 A | 9/1997 | Hara et al. |
| 5,747,053 A | 5/1998 | Nashimoto et al. |
| 5,766,595 A | 6/1998 | Yamane et al. |
| 5,795,911 A | 8/1998 | Cheng et al. |
| 5,804,567 A | 9/1998 | Cheng et al. |
| 5,807,564 A | 9/1998 | Shimamura et al. |
| 5,888,527 A | 3/1999 | Nashimoto et al. |
| 5,910,308 A | 6/1999 | D'Jang |
| 5,968,973 A | 10/1999 | Cheng et al. |
| 6,063,787 A | 5/2000 | Chu et al. |
| 6,096,359 A | 8/2000 | Bombardelli et al. |
| 6,127,393 A | 10/2000 | Fernandez-Pol |
| 6,197,808 B1 | 3/2001 | Cheng et al. |
| 6,210,679 B1 | 4/2001 | Bailey et al. |
| 6,248,341 B1 * | 6/2001 | Anderson et al. ............. 424/401 |
| 6,248,346 B1 | 6/2001 | Hara et al. |
| 6,337,320 B1 | 1/2002 | Hersh et al. |
| 6,372,234 B1 | 4/2002 | Deckers et al. |
| 6,399,046 B1 | 6/2002 | Schönrock et al. |
| 6,576,660 B1 | 6/2003 | Liao et al. |
| 6,596,763 B1 | 7/2003 | Thormar et al. |
| 6,696,484 B2 | 2/2004 | Liao et al. |
| 6,723,750 B2 * | 4/2004 | Voet ............................. 514/568 |
| 2002/0006447 A1 | 1/2002 | Yamazaki et al. |
| 2002/0031535 A1 | 3/2002 | Sheffield |
| 2002/0151582 A1 * | 10/2002 | Dou et al. ...................... 514/456 |
| 2002/0198161 A1 * | 12/2002 | Brash et al. ..................... 514/44 |
| 2003/0143165 A1 | 7/2003 | Evans et al. |
| 2003/0166583 A1 | 9/2003 | Yoa-Pu Hu et al. |
| 2004/0181130 A1 | 9/2004 | Miller et al. |
| 2004/0191842 A1 | 9/2004 | Hsu et al. |

(Continued)

FOREIGN PATENT DOCUMENTS

| DE | 199 62 369 | 6/2001 |
| EP | 0 087 161 | 8/1983 |
| EP | 0 244 457 | 6/1987 |

(Continued)

OTHER PUBLICATIONS

Bowen's disease from Wikipedia, accessed on May 22, 2014, pp. 1.*
Ahmad et al., "Green tea constituent epigallocatechin-3-gallate and induction of apoptosis and cell cycle arrest in human carcinoma cells," *J. Natl. Cancer Inst.* 89: 1881-1886 (1997). (Abstract).
American Chemical Society, *Chemical Abstracts*, vol. 80, Part 4: p. 319 (1974).
An et al., "Cyclooxygenase-2 expression in murine and human nonmelanoma skin cancers: implications for therapeutic approaches," *Photochemistry and photobiology* 76(1): 73-80 (2002).
Araki et al, "Chemoprevention of mammary preneoplasia. In vitro effects of green tea polyphenol," *Ann. N.Y. Acad. Sci.* 768: 215-222 (1995).

(Continued)

*Primary Examiner* — Qiuwen Mi
(74) *Attorney, Agent, or Firm* — Clark & Elbing LLP

(57) ABSTRACT

The present invention refers to a method for treating cancerous or precancerous lesions of the skin by administering a pharmaceutically effective amount of a polyphenol to a patient as well as to the production of a medicament thereto.

15 Claims, No Drawings

(56) References Cited

U.S. PATENT DOCUMENTS

| | | |
|---|---|---|
| 2005/0032895 A1 | 2/2005 | Chang et al. |
| 2005/0079235 A1 | 4/2005 | Stockfleth |

FOREIGN PATENT DOCUMENTS

| | | |
|---|---|---|
| EP | 0 573 682 A1 | 12/1993 |
| EP | 0 842 660 A1 | 5/1998 |
| EP | 1 005 862 A1 | 6/2000 |
| JP | A-10-147525 | 6/1998 |
| JP | A-2001-504461 | 4/2001 |
| WO | WO 98/20872 | 5/1998 |
| WO | WO 99/53916 | 10/1999 |
| WO | WO 99/66897 | 12/1999 |
| WO | WO 00/29027 | 5/2000 |
| WO | WO 00/33832 | 6/2000 |
| WO | WO 01/51048 | 7/2001 |
| WO | WO 2004/026323 A1 | 4/2004 |
| WO | WO 2004/053097 A2 | 6/2004 |

OTHER PUBLICATIONS

Beutner et al., "Patient-Applied Podofilox for Treatment of Genital Warts," *The Lancet* 1: 831-834 (1989).
Beutner et al., "Treatment of Genital Warts with an Immune-Response Modifier (Imiquimod)," *J. Am. Acad. Dermatol.* 38: 230-239 (1998).
Cao, "Angiogenesis Inhibited by Drinking Tea," *Nature* 398: 381 (1999).
Carter et al., "Drug-Tumor Interactions," in *Chemotherapy of Cancer* (Second Edition), pp. 361-379 (1981).
Ceve, "Drug Delivery Across the Skin," *Exp. Opin. Invest. Drugs* 6: 1887-1937 (1997).
CIR Compendium, p. 88 (1995) (Abstract).
Chow et al., "Pharmacokinetics and Safety of Green Tea Polyphenols after Multiple-Dose Administration of Epigallocatechin Gallate and Polyphenon E in Healthy Individuals," *Clinical Cancer Research* 9: 3312-3312 (2003).
Database STN Chemical Abstracts (XP-002123681) (1995).
David et al., "Novel approaches to chemoprevention of skin cancer," *J. Dermatol.* 27: 691-695, (2000).
Diding et al., "Isopropyl Myristate as Solvent in Sterility Testing of Petrolatum-Based Ointments," *Chemical Abstract* 19503q, pp. 616-621 (1973).
Edwards et al., "Self-Administered Topical 5% Imiquimod Cream for External Anogenital Warts," *Arch. Dermatol.* 134: 25-30 (1998).
Fulton et al., "Comedogenicity of Current Therapeutic Products, Cosmetics, and Ingredients in the Rabbit Ear," *J. Am. Acad. Dermatol.* 10:96-105 (1984) (English Language Abstract Only).
Garg et al., "Compendium of Pharmaceutical Excipients for Vaginal Formulations," *Pharm. Tech. Drug Delivery* pp. 14-24 (2001).
Greenberg et al., "A Double-Blind, Randomized Trial of 0.5% Podofilox and Placebo for the Treatment of Genital Warts in Women," *Obstetrics and Gynecology* 77: 735-739 (1991).
González de Mejía, "The Chemo-Protector Effects of Tea and Its Components," *Arch. Latinoam. Nutr.* 53:111-118 (2003) (English Language Abstract Only).
*Handbook of Pharmaceutical Excipients*, published by American Pharmaceutical Association and the Pharmaceutical Society of Great Britain p. 148 (1986).
Hara, "Antioxidants in Tea and Their Physiological Functions," in *Food and Free Radicals* Hiramatsu et al. (Eds.), Plenum Press (New York), pp. 49-65 (1997).
Jia et al., "Effects of Tea on Preneoplastic Lesions and Cell Cycle Regulators in Rat Liver," *Cancer Epidemiol. Biomarkers Prev.* 11: 1663-1667 (2002).
Katiyar et al., "Protection Against Induction of Mouse Skin Papillomas With Low and High Risk of Conversion to Malignancy by Green Tea Polyphenols," *Carcinogenesis* 18: 497-502 (1997).
Katiyar et al., "Green Tea and skin," *Arch. Dermatol*, 136: 989-994 (2000.).

Katiyar, "Skin photoprotection by green tea: antioxidant and immunomodulatory effects," *Curr. Drug Targets Immune Endocr. Metabol. Disord.* 3(3): 234-242 (2003).
Kirby et al., "Double-Blind Randomized Clinical Trial of Self-Administered Podofilox Solution Versus Vehicle in the Treatment of Genital Warts," *Am. J. Med.* 88: 465-469 (1990).
Kristmundsdottir et al., "Development and Evaluation of Microbicidal Hydrogels Containing Monoglyceride as the Active Ingredient," *J. Pharm. Sci.* 88: 1011-1015 (1999).
Li et al., "The Chemopreventive Effects of Tea on Human Oral Precancerous Mucosa Lesions," *Pro. Soc. Exp. Biol. Med.* 220(4) 218-224 (1999).
Linden et al., "Chemoprevention of Non-Melanoma Skin Cancer: Experience With a Polyphenol From Green Tea," *Eur. J. Cancer* 38: S24 (2002).
Linden et al., "Chemoprevention of Nonmelanoma Skin Cancer: Experience with a Polyphenol from Green Tea," *Recent Results in Cancer Res.* 163: 165-171 (2003).
Linden et al., "Epigallocatechin Gallate in the Chemoprevention of Non-Melanoma Skin Cancer, With Biomarker Studies of Actinic Keratoses, Sun-Damaged, and Non Sun Damaged Skin: Results of Clinical Trial," *Frontiers of in Cancer Prevention Research* A113, p. 29 (2003).
Lou et al, Effects of topical applications of caffeine or (−) epigallocatechin gallate (EGCG) on skin carcinogenesis and apoptosis in SKH-1 hairless mice previously treated with ultraviolet B light (high risk mice), *Proceedings of the American Association for Cancer Research*, 43: 1143, 2002.
Lu et al., "Effects of topical applications of caffeine or (−)-epigallocatechin gallate) EGCG on skin carcinogenesis and apoptosis in SKH-1 hairless mice previously treated with ultraviolet B light (high risk mice)," *Proceedings of the American Association for Cancer Research*, 43, #5664, p. 1143 (2002).
McCarty, "Polyphenol-Mediated Inhibition of AP-1 Transactivating Activity May Slow Cancer Growth by Impeding Angiogenesis and Tumor Invasiveness," *Medical Hypothesis* 50: 511-514 (1998).
Miura et al., "Effects of Various Natural Antioxidants on the $Cu^{2+}$-Mediated Oxidative Modification of Low Density Lipoprotein," *Biol. Pharm. Bull*.18: 1-4 (1995).
Mukhtar et al., "Green Tea Polyphenols Induce Apoptosis and Alter the Progression of Cell Cycle in Human Epidermoid Carcinoma Cells," *Proceedings of the American Association for Cancer Research and American Society of Clinical Oncology* 38: 580 (1997).
Mukhtar et al., "Green Tea in Chemoprevention of Cancer," *Toxicological Sciences* 52: 111-117 (1999).
Mukoyama et al., "Inhibition of Rotavirus and Enterovirus Infections by Tea Extracts," *Japanese Journal of Medical Science & Biology* 44: 181-186 (1991).
Nakayama et al., "Inhibition of the Infectivity of Influenza Virus by Tea Polyphenols," *Antiviral Research* 21: 289-299 (1993).
Perry et al., "Topical Imiquimod: A Review of its use in Genital Warts." *Drugs* 58(2): 375-390 (1999).
Pillai et al, "Antimutagenic/antioxidant activity of green tea components and related compounds," *J. Environ. Pathol. Toxicol, Oncol.* 18: 147-158 (1999). (Abstract).
Proniuk et al., "Preformulation Study of Epigallocatechin Gallate, a Promising Antioxidant for Topical Skin Cancer Prevention," *J. Pharm. Sci.* 91: 111-116 (2002).
Rice-Evans et al., "The Relative Antioxidant Activities of Plant-Derived Polyphenolic Flavonoids," *Free Radical Research* 22: 375-383 (1995).
Rösl et al., "Antioxidant-Induced Changes of the AP-1 Transcription Complex Are Paralleled by a Selective Suppression of Human Papillomavirus Transcription," *J. Virol.* 71: 362-370 (1997).
Sands et al., "Extreme Sensitivity of Enveloped Viruses, Including Herpes Simplex, to Long-Chain Unsaturated Monoglycerides and Alcohols," *Antimicrob. Agents Chemother.* 15: 67-73 (1979).
Telang et al., "Neoplastic Transformation of Mouse Mammary Epithelial Cells by Deregulated myc Expression," *Cell Regul.* 1: 863-872 (1990).
Toda et al., "The Bactericidal Activity of Tea and Coffee," *Letters in Applied Microbiology* 8: 123-125 (1989).

(56) References Cited

OTHER PUBLICATIONS

Toda et al., "Antibacterial and Anti-Hemolysin Activities of Tea Catechins and Their Structural Relatives," *Nippon Saikingaku Zasshi (Japanese Journal of Bacteriology)* 45: 561-566 (1990). Abstract only.

Tomita et al., "Tea and Its Components as Powerful Antioxidants," in *Oxidative Stress and Aging*, (Eds.), Birkhäuser Verlag (Basel, Switzerland), pp. 355-365 (1995).

Tyring et al., "Safety and Efficacy of 0.5% Podofilox Gel in the Treatment of Anogenital Warts," *Archives of Dermatology* 134: 33-38 (1998).

Wang et al., "Inhibitory effects of black tea, green tea, decaffeinated black tea, and decaffeinated green tea on ultraviolet B light-induced skin carcinogenesis in 7, 12-dimethylbenz[alpha] anthracene-initiated SKH-1 mice," *Cancer Research* 54: 3428-3435, (1994).

Yamane et al., "Skin Cosmetics Containing Tea Catechin," Chemical Abstract Database ICM A61K007, Japanese Patent No. 07196466 (Japanese Application No. 1993-352011) (1995).

Yanaga et al, "Prevention of carcinogenesis of mouse mammary epithelial cells RII/MG by epigallocatechin gallate," *Int. J. Mol. Med.* 10: 311-315 (2002).

Zhao et al., "Photoprotection in human skin by green tea and black tea," *Proceedings of the American Association for Cancer Research* 39: 382 (1998).

Zhao et al., "Photoprotective Effect of Black Tea Extracts Against UVB-induced Phototoxicity in Skin," *Photochemistry and Photobiology* 70: 637-644 (1999).

Zhu et al., "Study of Tea Polyphenol as a Reversal Agent for Carcinoma Cell Lines Multidrug Resistance (Study of TP as a MDR Reversal Agent," *Nuclear Medicine and Biology* 28: 735-740 (2001).

European Search Report for European Application No. 08021728, dated Mar. 26, 2010.

Office Action for U.S. Appl. No. 10/682,612, issued Jul. 28, 2006.
Office Action for U.S. Appl. No. 10/682,612, issued Jan. 29, 2007.
Office Action for U.S. Appl. No. 10/682,612, issued Aug. 3, 2007.
Office Action for U.S. Appl. No. 10/682,612, issued Jan. 30, 2008.
Office Action for U.S. Appl. No. 10/682,612, issued Oct. 21, 2008.
Office Action for U.S. Appl. No. 10/682,612, issued Jul. 7, 2009.
Office Action for U.S. Appl. No. 10/495,889, issued Sep. 21, 2007.
Office Action for U.S. Appl. No. 10/495,889, issued Jun. 27, 2008.
Office Action for U.S. Appl. No. 10/495,889, issued Feb. 25, 2009.

* cited by examiner

USE OF A POLYPHENOL FOR THE TREATMENT OF A CANCEROUS OR PRE-CANCEROUS LESION OF THE SKIN

CROSS REFERENCE TO RELATED APPLICATIONS

This application is a continuation of U.S. application Ser. No. 13/051,593, filed Mar. 18, 2011, which is a continuation of U.S. National stage application Ser. No. 10/574,422, filed Nov. 7, 2006, now U.S. Pat. No. 7,910,138, which claims priority to International Application No. PCT/EP2004/011300, filed Oct. 8, 2004, which claims benefit of U.S. Provision patent application 60/510,101, filed Oct. 9, 2003, all hereby incorporated by reference.

The present invention refers to a method for treating cancerous or pre-cancerous lesions of the skin by administering a pharmaceutically effective amount of a polyphenol to a patient as well as to the production of a medicament thereto.

Skin cancer is a disease in which malignant (cancer) cells are formed in the tissues of the skin. The skin is the body's largest organ. It protects against heat, sunlight, injury, and infection, helps to control the body temperature and stores water, fat, and vitamin D. The skin has several layers, but the two main layers are the epidermis (upper or outer layer) and the dermis (lower or inner layer). Skin cancer usually starts growing in the epidermis, which is made up of three kinds of cells. The squamous cells are thin, flat cells that form the top layer of the epidermis. The basal cells are round cells below the squamous cells and melanocytes are found in the lower part of the epidermis. These cells produce melanin, the pigment that is responsible for the natural color of the skin. When skin is exposed to the sun, melanocytes are induced to produce more pigment causing the skin to tan or darken.

Skin cancer can occur anywhere but it is most common iii skin that has been exposed to sunlight, such as the face, ears, neck, bald scalp, hands, shoulders, arms and/or the back. There are several types of cancer that start in the skin. The most common types are basal cell carcinoma and squamous cell carcinoma which are non melanoma skin cancers. Actinic keratosis is a skin condition that sometimes develops into squamous cell carcinoma.

Basal cell carcinoma or basalioma is the most common form of skin cancer affecting 800,000 Americans each year. In fact, it is the most common of all cancers. One out of every three new cancers is a skin cancer and the vast majority are basal cell carcinomas often referred to by the abbreviation, BCC. These cancers arise in the basal cells which are at the bottom of the epidermis (outer skin layer). Until recently, those people which were most often affected, were older people, particularly men who had worked outdoors. Although the number of new cases has increased sharply each year in the last few decades, the average age of onset of the disease has steadily decreased. More women are getting BCC than in the past. Nonetheless, men still outnumber them greatly. Chronic exposure to sunlight is the cause of almost all basal cell carcinomas which occur most frequently on exposed parts of the body. Rarely, however, tumors develop on non-exposed areas. In a few cases, contact with arsenic, exposure to radiation and complications of burns, scars, vaccinations or even tattoos are contributing factors.

Squamous cell carcinoma (SCC), the second most common skin cancer after basal cell carcinoma, afflicts more than 200,000 Americans each year. It arises from the epidermis and resembles the squamous cells that comprise most of the upper layers of skin. Squamous cell cancers may occur on all areas of the body including the mucous membranes, but are most common in areas exposed to the sun. Although squamous cell carcinomas usually remain confined to the epidermis for some time, they eventually penetrate the underlying tissues if not treated. In a small percentage of cases they spread (metastasize) to distant tissues and organs which can be fatal for the person afflicted. Metastasing squamous cell carcinomas most often arise on sites of chronic inflammatory skin conditions or on the mucous membranes or lips. Chronic exposure to sunlight causes most cases of squamous cell carcinoma because tumors appear most frequently on sun-exposed parts of the body. The rim of the ear and the lower lip are especially vulnerable to the development of these cancers. Squamous cell carcinomas may also occur where skin has suffered certain kinds of injury such as burns, scars, long-standing sores, sites previously exposed to X-rays and/or certain chemicals such as arsenic and petroleum by-products. In addition, chronic skin inflammation or medical conditions that suppress the immune system over an extended period of time may encourage development of squamous cell carcinoma. Occasionally, squamous cell carcinoma arises spontaneously on what appears to be normal, healthy or undamaged skin. Some researchers believe that a tendency to develop this cancer may be inherited.

Certain precursor conditions, some of which result from extensive sun damage, are sometimes associated with the later development of squamous cell carcinoma. They include actinic keratoses, actinic cheilitis, leukoplakia and Bowen's disease.

Actinic keratosis (AK), also known as a solar keratosis, arises on the skin surface. AK appears as rough, scaly crusty and/or slightly raised growths that range in color from brown to red and may be up to one inch in diameter. It appears most often in older people. The base may be light or dark, tan, pink, red or a combination of these or has the same color as the skin itself. The scale or crust is horny, dry and rough and is often recognized by touch rather than sight. Occasionally, it itches or produces a pricking or tender sensation. It can also become inflamed and surrounded by redness. In rare instances, actinic keratoses can even bleed. The skin abnormality or lesion develops slowly and generally reaches a size from an eighth to a quarter of an inch. Early on, it may disappear only to reappear later. Several Aks can often been seen at a time and are most likely to appear on the parts of the body most often exposed to sunshine. The growths may be flat and pink or raised and rough. AK can be the first step in the development of skin cancer. It is thus a precursor of cancer or a precancer. If treated early, almost all AKs can be eliminated without becoming skin cancers. But untreated, about two to five percent of these lesions may progress to squamous cell carcinomas. In fact, some scientists now believe that AK is the earliest form of Squamous Cell Carcinoma (SCC). These cancers are usually not life-threatening, provided they are detected and treated in the early stages. However, if this is not done, they can grow large and invade the surrounding tissues and on rare occasions, metastasize or spread to the internal organs.

Actinic cheilitis is another form of actinic keratosis which occurs on the lips and causes them to become dry, cracked, scaly and pale or white. It mainly affects the lower lip, which typically receives more sun exposure than the upper lip, and may evolve into a type of SCC that can spread rapidly to other parts of the body.

Chronic sun exposure is the cause of almost all AKs. Sun damage to the skin accumulates over time, so that even a brief exposure adds to the lifetime total. The likelihood of developing AK is highest in regions near the equator. However, regardless of climate, everyone is exposed to the sun. About 80 percent of solar UV rays can pass through clouds. These rays can also bounce off sand, snow and other reflective surfaces giving you extra exposure. AKs can also appear on skin that has been frequently exposed to artificial sources of UV light, such as tanning devices. More rarely, they may be caused by extensive exposure to X-rays or specific industrial chemicals. Individuals whose immune systems are weakened as a result of cancer chemotherapy, AIDS or organ transplantation are also at higher risk. AK is the most common type of precancerous skin lesion. Older people are more likely than younger ones to develop these lesions because cumulative sun exposure increases with the years. Some experts believe that the majority of people who live to the age of 80 will have AK.

Leukoplakia, another precursor condition, are white patches on the tongue or inside of the mouth having the potential to develop into squamous cell carcinoma.

Bowen's disease is generally considered to be a superficial squamous cell cancer that has not yet spread. It appears as a persistent red-brown, scaly patch which may resemble psoriasis or eczema. If untreated, it may invade deeper structures.

The standard therapies used in pre-cancerous or cancerous lesions of the skin might not be applicable in all patients, e.g. surgery in patients with severe concomitant diseases, or have severe side-effects and may result in skin breakdown, discoloration, irritation, damage to surrounding normal skin, swelling and/or scars.

Consequently, the problem underlying the present invention resides in providing an alternative therapy for pre-cancerous or cancerous lesions of the skin for at least most of the group of patients.

Surprisingly, it has been found that the treatment of the skin with at least one polyphenol, in particular with at least one catechin elicits a positive effect on pre-cancerous or cancerous lesions of the skin.

One subject-matter of the present invention is, therefore, a method for treating a cancerous, including pre-cancerous, lesion of the skin by administering a pharmaceutically effective amount of a polyphenol or a mixture of polyphenols to a patient, in particular to a human.

In a preferred embodiment the lesion of the skin is a non-virally induced lesion, in particular a lesion not caused by a papilloma virus, preferably not a lesion selected from hyperplasia, Condyloma acuminata, warts, including without limitation common warts and/or plantar warts, and/or cervical intra-epithelial neoplasia.

According to the present invention, the term "non-virally induced cancerous lesion" means a cancerous and/or pre-cancerous condition of the skin which is not caused or induced by viruses which can infect the skin, such as papilloma viruses, in particular human papilloma viruses, e.g. HPV 1, 2, 3, 4, 5, 6, 8, 9, 11, 12, 13, 14, 15, 16, 17, 18, 19-29, 31, 32, 34, 36-38, 46-50 and/or 56-58, and/or herpes viruses, such as herpes simplex virus 1, herpes simplex virus 2, varicella zoster virus and/or human herpes virus, such as HHV 1, 2, 3, 4, 7 and/or 8. Examples of diseases caused or induced by viruses are verrucae plantares, verrucae vulgares, verrucae planae juveniles, epidermodysplasia verruciformis, Condylomata acuminata, Condylomata plana, bowenoid papulosis, papillomas on the larynx and oral mucosa, focal epithelial hyperplasia, herpes labialis, Kaposi's sarcoma, varicella and shingles.

The term "pharmaceutically effective amount" means an amount of at least one polyphenol which causes a positive effect on the lesion of the skin of the patient, e.g. causes a reduction or disappearance of the lesion, in particular with the aim to improve or cure the disease of the patient. Pharmaceutically effective amounts are e.g. formulations, preferably ointments, containing about 2% (w/w) to about 50% (w/w), especially about 5% (w/w) to about 20% (w/w), in particular about 10% (w/w) to about 15% (w/w) and most preferred about 10% (w/w) or about 15% (w/w) of at least one polyphenol or of a mixture of several (different) polyphenols. These amounts can be applied once or several times, e.g. 3 to 5 times a week for 6 to 12 weeks, until the positive effect on the lesion of the skin of the patient occurs.

The term "about" means according to the invention a general error range of +/−20%, especially +/−10%, in particular +/−5%.

Polyphenols are naturally occurring phenolic compounds, preferably with 1, 2 or 3 aromatic rings, in particular with 2 aromatic rings, carrying at least two hydroxyl groups, such as catechols, flavons, flavonoids and/or anthocyanidins, e.g. pelargonidin, cyanidin, delphinidin, paonidin, petunidin, malvidin and/or hirsutidin, whereas catechols are naturally occurring polyphenols usually found in resins and/or lignins. Alternative names used in the literature for catechols are catechins, pyrocatechols or 1,2-dihydroxybenzenes.

The polyphenols, in particular the catechols employed in the present invention may be obtained either synthetically or from natural sources. The natural sources which may especially be mentioned are tea plants, in particular green tea. In this context, the natural constituents may be present in differing concentrations depending on the species and variety. In this connection, the polyphenols, in particular the catechols which are employed are preferably isolated or extracted from Camellia sinensis, Camellia asamica, Camellia bohea, Camellia chinensis and/or Camellia oleosa. All the components of tea plants, in particular the leaves, can be used for isolating or extracting the polyphenols, in particular the catechols. The polyphenols, in particular the catechols which are employed are preferably isolated from a tea extract, in particular from a green tea extract or easily extracted from a tea, in particular from a green tea. Suitable methods for the isolation or extraction of polyphenols, in particular catechols are described e.g. in U.S. Pat. No. 4,613,672, U.S. Pat. No. 4,673, 530, U.S. Pat. No. 4,913,909, U.S. Pat. No. 6,096,359 or U.S. Pat. No. 4,248,789.

Generally, the polyphenols have the formula (I)

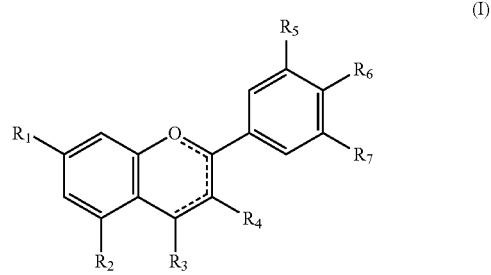

(I)

in which $R_1$, $R_2$ and $R_6$ are independently from each other —H or —OH, $R_3$ is —H or =O, $R_4$ is independently from each other —H, —OH or a group of the formula (III)

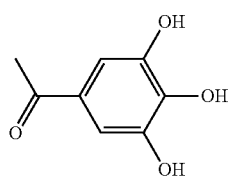

$R_5$ and $R_7$ are independently from each other —H, —OH or —OCH$_3$, and

---- optionally represents a bond, and the catechols have the formula (II)

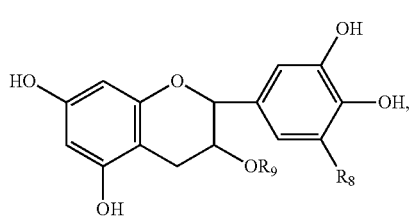

in which $R_8$ is —H or —OH, and $R_9$ is —H or a group of the formula (III)

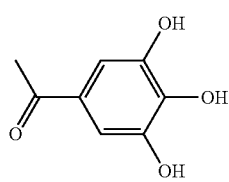

Examples of polyphenols are:

Polyphenol derivatives of flavan with the formula (IV):

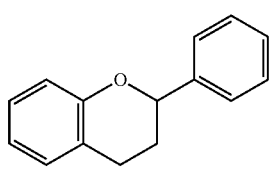

Polyphenol derivatives of flavan-3-ol with the formula (V):

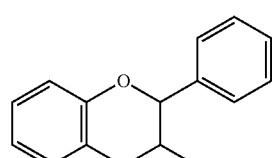

Polyphenol derivatives of flavanon with the formula (VI):

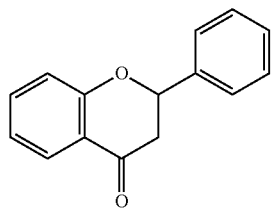

Polyphenol derivatives of flavon with the formula (VII):

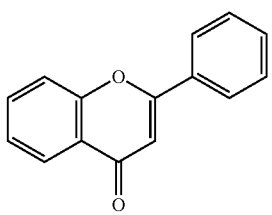

Polyphenol derivatives of flavonol with the formula (VIII):

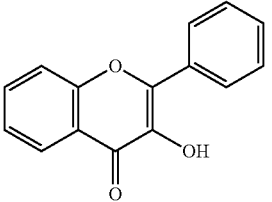

Polyphenol derivatives of chalcon with the formula (IX):

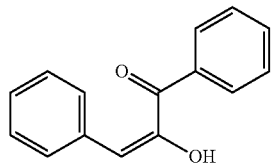

and anthocyanidins with the formula (X):

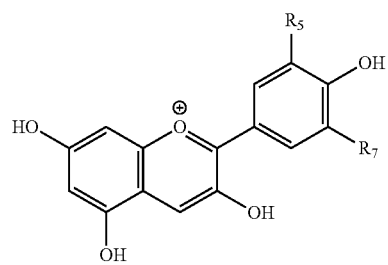

with $R_5$ and $R_7$ are independently from each other —H, —OH or —OCH$_3$, as e.g. in pelargonidin, cyanidin, delphinidin, paonidin, petunidin, malvidin or hirsutidin.

Preferably, the catechol is selected from catechol, catechol gallate, epicatechol, epicatechol gallate, epigallocatechol, epigallocatechol gallate, gallocatechol and/or gallocatechol gallate and in particular from (+)-catechol, (−)-catechol, (+)-catechol gallate, (−)-catechol gallate, (+)-epicatechol, (−)-epicatechol, (+)-epicatechol gallate, (−)-epicatechol gallate, epigallocatechol, (−)-epigallocatechol, (+)-epigallocatechol gallate, (−)-epigallocatechol gallate, (+)-gallocatechol, (−)-gallocatechol, (+)-gallocatechol gallate and (−)-gallocatechol gallate.

The structural formula of the most preferred catechols are:

For (−)-epigallocatechol gallate (−)-EGCG:

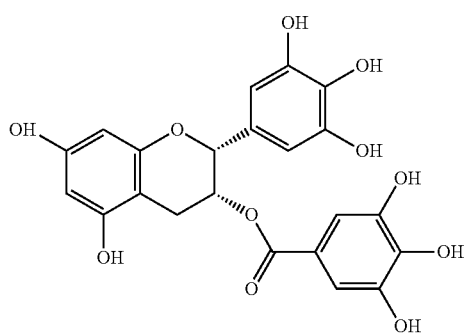 [SMILES: O=C(O[C@@H]1Cc2c(O)cc(O)cc2O[C@@H]1c1cc(O)c(O)c(O)c1)c1cc(O)c(O)c(O)c1]

For (−)-epigallocatechol (−)-EGC:

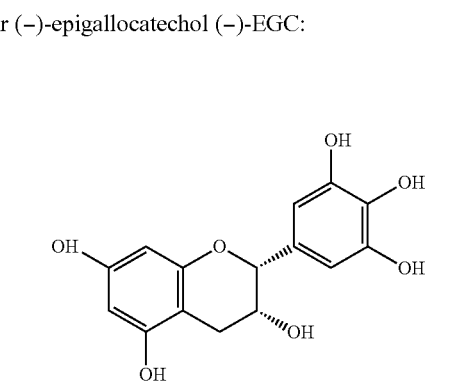

For (−)-epicatechol gallate (−)-ECG:

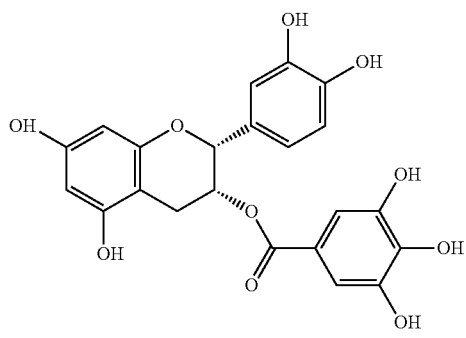 [SMILES: O=C(O[C@@H]1Cc2c(O)cc(O)cc2O[C@@H]1c1ccc(O)c(O)c1)c1cc(O)c(O)c(O)c1]

For (−)-epicatechol (−)-EC:

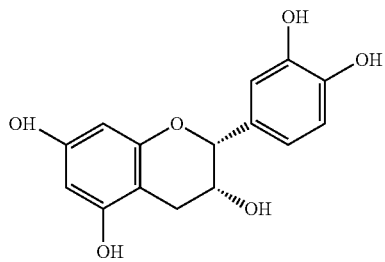 [SMILES: Oc1cc(O)c2c(c1)O[C@H](c1ccc(O)c(O)c1)[C@H](O)C2]

For (+)-epicatechol (+)-EC:

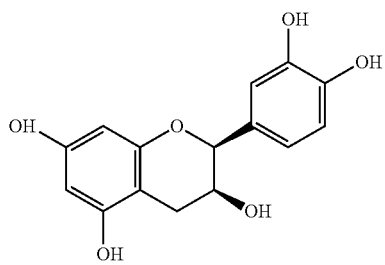 [SMILES: Oc1cc(O)c2c(c1)O[C@@H](c1ccc(O)c(O)c1)[C@@H](O)C2]

For (+)-catechol (+)-C:

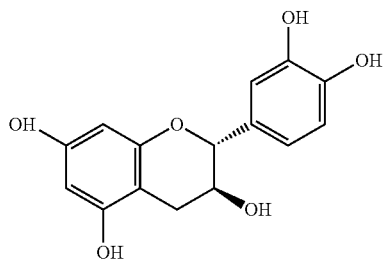 [SMILES: Oc1cc(O)c2c(c1)O[C@H](c1ccc(O)c(O)c1)[C@@H](O)C2]

For (−) catechol (−)-C:

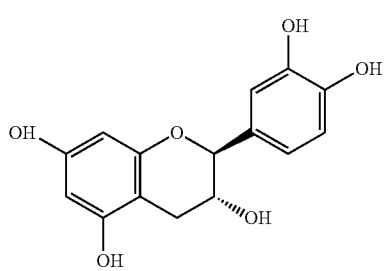 [SMILES: Oc1cc(O)c2c(c1)O[C@@H](c1ccc(O)c(O)c1)[C@H](O)C2]

For (−)-gallocatechol gallate (−)-GCG:

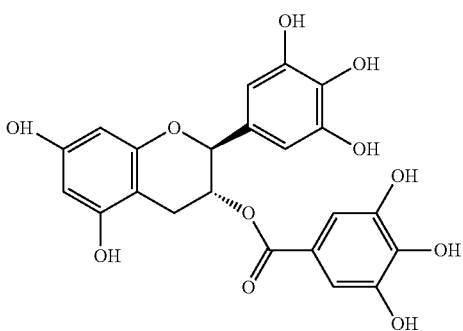 [SMILES: O=C(O[C@@H]1Cc2c(O)cc(O)cc2O[C@H]1c1cc(O)c(O)c(O)c1)c1cc(O)c(O)c(O)c1]

For (−)-catechol gallate (−)-CG:

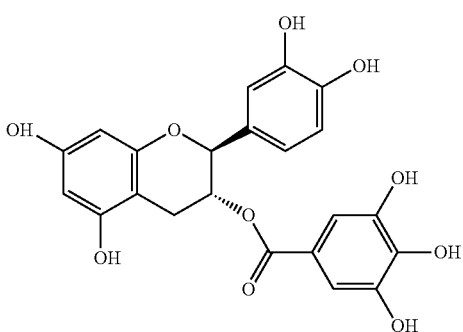 [SMILES: O=C(O[C@@H]1Cc2c(O)cc(O)cc2O[C@H]1c1ccc(O)c(O)c1)c1cc(O)c(O)c(O)c1]

For (+)-gallocatechol (+)-GC:

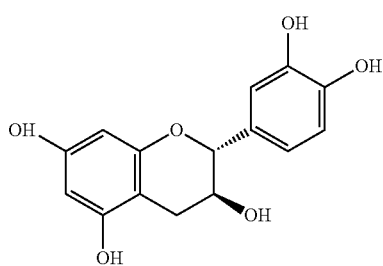

For (−)-gallocatechol (−)-GC:

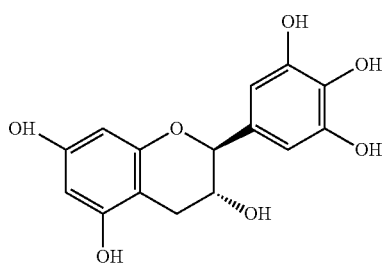 [SMILES: Oc1cc(O)c2c(c1)O[C@@H](c1cc(O)c(O)c(O)c1)[C@H](O)C2]

In another particularly preferred embodiment of the present invention the polyphenols, in particular the catechols, are present in the form of a mixture of polyphenols, in particular catechols, especially containing catechol, catechol gallate, epicatechol, epicatechol gallate, epigallocatechol, epigallocatechol gallate, gallocatechol and/or gallocatechol gallate, preferably in the stereochemistry as defined above. The preferred catechols are in particular the gallates of catechol, epicatechol, epigallocatechol or of gallocatechol, as they are generally more active as the catechols. In particular, the present invention is directed to mixtures of the particular gallates containing more than about 40% (w/w), preferably more than about 50% (w/w), especially more than about 60% (w/w) and in particular more than 65% (w/w) of the particular gallates. These gallates may be (−) or (+) stereoisomers wherein the (−) stereoisomers are preferred.

Preferred catechols employed in the present invention are (−)-epicatechol, (−)-epicatechol gallate, (−)-epigallocatechol, (−)-epigallocatechol gallate, (+)-gallocatechol and/or (−)-gallocatechol gallate, in particular in form of a mixture containing about 2-20% (w/w) epicatechol, about 2-20% (w/w), epicatechol gallate, about 1-25% (w/w) epigallocatechol, about 40-75% (w/w) epigallocatechol gallate, about 0.05-5% (w/w) gallocatechol and/or about 0.5-20% (w/w) gallocatechol gallate, especially a mixture containing about 10.8% (w/w) of epicatechol, about 6.5% (w/w) of epicatechol gallate, about 9.2% (w/w) of epigallocatechol, about 54.8% (w/w) of epigallocatechol gallate and/or about 4.0% (w/w) of gallocatechol gallate, all of them preferably in the stereochemistry as defined above, in particular in form of a mixture containing about 10.8% (w/w) of (−)-epicatechol, about 6.5% (w/w) of (−)-epicatechol gallate, about 9.2% (w/w) of (−)-epigallocatechol, about 54.8% (w/w) of (−)-epigallocatechol gallate and/or about 4.0% (w/w) of (−)-gallocatechol gallate.

Alternatively, the mixture of catechols contains about 2-12% (w/w), preferably about 5-8% (w/w) epicatechol, about 4-15% (w/w), preferably about 5-7% (w/w), in particular about 5-6% (w/w) epicatechol gallate, about 1-8% (w/w), preferably about 2-3% (w/w), in particular about 6-8% (w/w) epigallocatechol, about 60-68% (w/w), preferably about 61-65% (w/w) epigallocatechol gallate, about 0.05-1% (w/w) gallocatechol and about 1-7% (w/w), preferably about 2-4% (w/w) gallocatechol gallate.

Consequently, the catechols can be used both individually and in the form of mixtures having different compositions as specified above. For example, a composition known under the tradename Polyphenon® 100 is composed of about 5.9% (w/w) of (−)-epicatechol, about 12.6% (w/w) of (−)-epicatechol gallate, about 17.6% (w/w) of (−)-epigallocatechol, about 53.9% (w/w) of (−)-epigallocatechol gallate and/or about 1.4% (w/w) of (−)-gallocatechol. As another example, a composition known under the tradename Polyphenon© E is composed of about 10.8% (w/w) of (−)-epicatechol, about 6.5% (w/w) of (−)-epicatechol gallate, about 9.2% (w/w) of (−)-epigallocatechol, about 54.8% (w/w) of (−)-epigallocatechol gallate and/or about 4.0% (w/w) of (−)-gallocatechol gallate.

The familiar methods of pharmaceutical technology are used, in a customary manner, for preparing pharmaceuticals which comprise one or more compounds according to the present invention and/or for using these pharmaceuticals in the application according to the invention. For this, the active compounds are worked up, together with one or more suitable, pharmaceutically acceptable additives, if necessary, into the medicinal forms which are suitable for the different indications and sites of administration. In this context, the pharmaceuticals can be prepared such that the rate of release in each case desired, for example a rapid accumulation and/or a delayed-release or depot effect, is achieved.

Consequently, another embodiment of the present invention is directed to the use of a pharmaceutical effective amount of a polyphenol, in particular a catechol or a mixture of (different) polyphenols, in particular catechols, as specified above, for the production of a medicament for the treatment of cancerous, including pre-cancerous, lesions of the skin, preferably a non-virally induced lesion, in particular a lesion not caused by a papilloma virus, preferably not a lesion selected from hyperplasia, Condyloma acuminata, warts, including without limitation common warts and/or plantar warts, and/or cervical intra-epithelial neoplasia, as explained therein, preferably for the topical administration of the polyphenol, in particular catechol, or polyphenol, in particular catechol mixture.

Examples of suitable additives are sodium alginate, as a gelatinizing agent for preparing a suitable base, or cellulose derivatives, such as guar or xanthan gum, inorganic gelatinizing agents, such as aluminum hydroxide or bentonites (what are termed thixotropic gel-formers), polyacrylic acid derivatives, such as Carbopol®, polyvinylpyrrolidone, microcrystalline cellulose and carboxymethylcellulose. Amphiphilic low molecular weight and higher molecular weight compounds, and also phospholipids, are also suitable. The gels can be present either as water-based hydrogels or as hydrophobic organogels, for example based on mixtures of low and high molecular weight paraffin hydrocarbons and vaseline. The hydrophilic organogels can be prepared, for example, on the basis of high molecular weight polyethylene glycols. These gelatinous forms are washable. However, the organogels which are preferred are the hydrophobic organogels. Particular preference is given to hydrophobic additives, such as petroleum jelly, wax, oleyl alcohol, propylene glycol monostearate and/or propylene glycol monopalmitostearate, in particular isopropyl myristate. It is, of course, likewise possible to add skin-sedating and/or inflammation-inhibiting additives which are known to the skilled person, such as synthetically prepared active compounds and/or extracts and/or active compounds from medicinal plants, in particular bisobolol and panthenol. It is furthermore also possible to add dyes, for example yellow and/or red iron oxide and/or titanium dioxide for the purpose of matching as regards color.

Generally, the polyphenol, in particular the catechol or mixture of polyphenols, in particular catechols, is contained in a carrier, e.g. in the form of an emulsion, a gel, a cream or an ointment.

Customary emulsions, gels, creams and ointments of the mixed-phase or amphiphilic emulsion systems (oil/water-water/oil mixed phase), and also liposomes and transfersomes or plasters, preferably ointments and creams, particularly preferably an ointment, may be mentioned for conventional application to the skin. The catechol is preferably applied locally in the region in which there is a cancerous or pre-cancerous skin lesion.

Emulsifiers which can be employed are anionic, cationic or neutral surfactants, for example alkali metal soaps, metal soaps, amine soaps, sulphurated and sulphonated compounds, invert soaps, higher fatty alcohols, partial fatty acid esters of sorbitan and polyoxyethylene sorbitan, e.g. lanette types, wool wax, lanolin or other synthetic products for preparing the oil/water and/or water/oil emulsions.

It is possible to use vaseline, natural or synthetic waxes, fatty acids, fatty alcohols, fatty acid esters, for example as monoglycerides, diglycerides or triglycerides, paraffin oil or vegetable oils, hydrogenated castor oil or coconut oil, hog fat, synthetic fats, for example based on, caprylic acid, capric acid, lauric acid or stearic acid, such as Softisan®, or triglyceride mixtures, such as Miglyol®, can be used as lipids, in the form of fatty and/or oleaginous and/or waxy components for preparing the ointments, creams or emulsions.

It is possible to use, for example, osmotically active acids and alkaline solutions, for example hydrochloric acid, citric acid, sodium hydroxide solution, potassium hydroxide solution, sodium hydrogen carbonate, and, in addition, buffer systems, such as citrate, phosphate, tris buffer or triethanolamine, for adjusting the pH. It is possible to add preservatives as well, such as methyl benzoate or propyl benzoate (parabens) or sorbic acid, for increasing the stability.

Pastes, powders and solutions may be mentioned as additional forms which can be applied topically. As consistency-imparting bases, the pastes frequently contain hydrophobic and hydrophilic auxiliary substances, preferably, however, hydrophobic auxiliary substances containing a very high proportion of solids. In order to increase dispersity, and also flowability and slipperiness, and also to prevent agglomerates, the powders or topically applicable powders can, for example, contain starch species, such as wheat or rice starch, flame-dispersed silicon dioxide or siliceous earth, which also serve as diluent.

The medicinal forms which are in each case suitable can be produced on the basis of pharmaceutico-physical principles in conformity with formulation guidelines and methods known to a skilled person.

As a further example, the pharmaceutical employed in the present invention preferably comprises about 35% (w/w) of isopropyl myristate, about 15% (w/w) of at least one catechol, about 24.5% (w/w) of petroleum jelly, about 20% (w/w) of wax, about 5% (w/w) of propylene glycol monostearate or propylene glycol monopalmitostearate and about 0.5% (w/w) of oleyl alcohol.

An alternative embodiment of the present invention is directed to a combination therapy.

Therefore, the present invention also encompasses a method for treating a cancerous, including pre-cancerous, lesion of the skin, preferably a non-virally induced lesion, in particular a lesion not caused by a papilloma virus, preferably not a lesion selected from hyperplasia, Condyloma acuminata, warts, including without limitation common warts and/or plantar warts, and/or cervical infra-epithelial neoplasia, as explained therein, by administering a pharmaceutically effective amount of a catechol or a mixture of catechols, as specified above, in combination with a different anticancer treatment and the preparation of a corresponding medicament. The administration of the different anticancer agent can be simultaneous with, prior to or after the administration of the polyphenol, in particular catechol or the mixture of polyphenols, in particular catechols.

According to the present invention the term "different anticancer treatment" refers preferably to surgery, electrodessication, curettage, excision, Mohs micrographic surgery, radiation, proton therapy, chemotherapy, photodynamic therapy, cryosurgery, laser, immunotherapy, vaccine therapy and/or biologic therapy. Preferred chemotherapeutic treatments encompass the use of podophyllin, 5-fluorouracil, bleomycin, interferon or imiquimod, and mixtures thereof. A preferred radiotherapy is X-ray radiation and/or γ-radiation.

The skin lesions referred to in the present invention are preferably skin cancer or cutaneous carcinoma, basal cell carcinoma, squamous cell carcinoma, actinic or solar keratosis, epithelioma or epithelial tumors, skin neoplasm, Bowen's disease, acanthoma, cancroid, cutaneous horn, hyperkeratosis, keratosis, molluscum contagiosum, lid tumors, xanthelasma, xanthoma, fibroma, verucca senilis, seborrheic keratosis, cheilocarcinoma, papillomatosis, penis carcinoma, radiodermatitis, sailor's skin, tar cancer, vaginal carcinoma, vulvar cancer, erythroplasia queyrat and/or carcinoma of the tongue. In particular, the skin lesions are actinic or solar keratosis and/or basal cell carcinoma.

Taken together, one of the most preferred embodiments of the present invention is the use of a pharmaceutical formulation containing a mixture of different polyphenols as disclosed above in an amount of about 10% (w/w) to about 15% (w/w) in the pharmaceutical formulation for the treatment of actinic keratosis, solar keratosis and/or basal cell carcinoma. The mixture of different polyphenols contains in particular more than 60% (w/w), especially more than 65% (w/w) gallates of catechol, epicatechol, epigallocatechol or of gallocatechol. Preferred mixtures of different polyphenols are Polyphenon® 100 or Polyphenon® E as specified above. Finally, a preferred pharmaceutical formulation comprises about 35% (w/w) of isopropyl myristate, about 15% (w/w) of at least a mixture of different polyphenols as specified in this paragraph, in particular Polyphenon® 100 or Polyphenon® E, about 24.5% (w/w) of petroleum jelly, about 20% (w/w) of wax, about 5% (w/w) of propylene glycol monostearate or propylene glycol monopalmitostearate and about 0.5% (w/w) of oleyl alcohol which can be used in the treatment of actinic keratosis, solar keratosis and/or basal cell carcinoma.

The following examples are intended to clarify the invention without restricting it. Skilled persons can modify the invention appropriately, within the bounds of customary ability, without departing from the protective scope.

EXAMPLE 1

Patient: 65 years old, male with actinic keratoses known since 10 years;
The patient was treated with Polyphenon® E (15% ointment containing 35% (w/w) isopropyl myristate, 15% (w/w) catechol extract, 24.5% (w/w) petroleum jelly, 20% (w/w) wax, 5% (w/w) propylene glycol monostearate and 0.5% (w/w) oleyl alcohol):
Treated area: about 5 cm² on the forehead
Treatment schedule: 5 times a week (each with 10 hours)
Treatment period: 6 weeks
Treatment Progression:
  after about 13 days of treatment skin irritation of the treated area (more precisely treated areas afflicted by actinic keratoses) occurred
  also an up-regulation of subclinical lesions occurred
  skin irritation ameliorated during further treatment
  after 12 weeks of treatment actinic keratoses have disappeared completely

EXAMPLE 2

Patient: 73 years old, male with actinic keratoses known since about 15 years, multiply pre-treated;
The patient was treated with Polyphenon® E (15% ointment containing 35% (w/w) isopropyl myristate, 15% (w/w) catechol extract, 24.5% (w/w) petroleum jelly, 20% (w/w) wax, 5% (w/w) propylene glycol monostearate and 0.5% (w/w) oleyl alcohol):
Treated area: about 5 cm² on the head
Treatment schedule: 3 times a week
Treatment period: 12 weeks
Treatment Progression:
  after 3.5 weeks of treatment skin irritation of the treated area afflicted by actinic keratoses occurred (but less intense than that of the patient of Example 1)
  after 12 weeks of treatment only single actinic keratoses have been left and after 16 weeks of treatment actinic keratoses have disappeared completely

The invention claimed is:

1. A method for treating a lesion of the skin of a patient, wherein said lesion is Bowen's disease or verucca senilis, said method comprising topically administering to the skin lesion a pharmaceutically effective amount of a polyphenol composition comprising (i) a mixture of polyphenols and (ii) a carrier, wherein the composition comprises from about 5% (w/w) to about 20% (w/w) of the mixture of polyphenols, wherein the mixture of polyphenols contains epicatechol, epicatechol gallate, epigallocatechol, epigallocatechol gallate, and gallocatechol gallate.

2. The method according to claim 1, wherein the patient is a human.

3. The method according to claim 1, wherein the polyphenol is isolated from tea or a tea extract.

4. The method according to claim 3, wherein the tea is a green tea.

5. The method according to claim 3, wherein the tea extract is a green tea extract.

6. The method according to claim 1, wherein the mixture of polyphenols contains (−)-epicatechol, (−)-epicatechol gallate, (−)-epigallocatechol, (−)-epigallocatechol gallate, and (−)-gallocatechol gallate.

7. The method according to claim 1, wherein the mixture of polyphenols contains about 2-20% (w/w) epicatechol, about 2-20% (w/w) epicatechol gallate, about 1-25% (w/w) epigallocatechol, about 40-75% (w/w) epigallocatechol gallate, and about 0.5-20% (w/w) gallocatechol gallate.

8. The method according to claim 7, wherein the mixture of polyphenols contains about 10.8% (w/w) of (−)-epicatechol, about 6.5% (w/w) of (−)-epicatechol gallate, about 9.2% (w/w) of (−)-epigallocatechol, about 54.8% (w/w) of (−)-epigallocatechol gallate, and about 4.0% (w/w) of (−)-gallocatechol gallate.

9. The method according to claim 1, wherein the mixture of polyphenols is combined with an additive.

10. The method according to claim 9, wherein the additive is selected from the group consisting of petroleum jelly, wax, oleyl alcohol, propylene glycol monostearate, propylene glycol monopalmitostearate, and isopropyl myristate.

11. The method according to claim 1, wherein the polyphenol composition contained in a carrier is selected from the group consisting of an emulsion, a gel, a cream, and an ointment.

12. The method according to claim 1, wherein the method for treating said lesions is combined with a different anticancer treatment.

13. The method according to claim 12, wherein the different anticancer treatment is selected from the group consisting of surgery, electrodessication, curettage, excision, Mohs micrographic surgery, radiation, proton therapy, chemotherapy, photodynamic therapy, cryosurgery, laser, immunotherapy, vaccine therapy, and biologic therapy.

14. The method according to claim 1, wherein the composition comprises about 15% (w/w) mixture of polyphenols.

15. A method for treating a lesion of the skin in a patient, wherein said skin lesion is Bowen's disease or verucca senilis, said method comprising topically administering a pharmaceutically effective amount of a polyphenol composition comprising (i) a mixture of polyphenols and (ii) a carrier, wherein the composition comprises about 15% (w/w) mixture of polyphenols, wherein the mixture of polyphenols contains about 10.8% (w/w) of (−)-epicatechol, about 6.5% (w/w) of (−)-epicatechol gallate, about 9.2% (w/w) of (−)-epigallocatechol, about 54.8% (w/w) of (−)-epigallocatechol gallate, and about 4.0% (w/w) of (−)-gallocatechol gallate.

* * * * *